United States Patent [19]

Dunn et al.

[11] Patent Number: 4,759,350
[45] Date of Patent: Jul. 26, 1988

[54] INSTRUMENTS FOR SHAPING DISTAL FEMORAL AND PROXIMAL TIBIAL SURFACES

[76] Inventors: Harold K. Dunn, 1231 Chandler Cir.; Kim C. Bertin, 666 Northcliffe Cir., both of Salt Lake City, Utah 84103

[21] Appl. No.: 919,971
[22] Filed: Oct. 17, 1986
[51] Int. Cl.⁴ .............................................. A61F 5/04
[52] U.S. Cl. ............................................ 128/92 VW
[58] Field of Search ......... 128/92 VW, 92 V, 92 VY; 623/39

[56] References Cited

U.S. PATENT DOCUMENTS 4,524,766  6/1985  Petersen .................. 128/92 VW
4,646,729  3/1987  Kenna et al. ............. 128/92 VW

FOREIGN PATENT DOCUMENTS 0121786  10/1984  European Pat. Off. ....... 128/92 VW

OTHER PUBLICATIONS

Howmedica Catalog, 1984.
A.O.R. Catalog.
Zimmer Catalog, 1986.
Johnson and Johnson Catalog, 1984.
Dow Corning Wright Catalog, 1984.
R.M.C. Catalog, 1978.
Insall/Burstein Total Condylar Knee System, 1981.

*Primary Examiner*—C. Fred Rosenbaum
*Assistant Examiner*—Mark Colosimo
*Attorney, Agent, or Firm*—M. Reid Russell

[57] ABSTRACT

The present invention provides a system of instruments for shaping the distal femur and proximal tibia surfaces to receive components of a knee prosthesis for knee replacement surgery. The system references the femur intramedullary channel with a femoral alignment guide to prepare the distal femur that, in turn, is a reference for several cutting guides for sequential attachment to the femoral alignment guide and prepared bone surfaces whereby the prepared distal femur is prepared to a flat surface that is perpendicular to the patient's mechanical axis with bone surfaces adjacent thereto sectioned to surfaces that are at right angles to that distal femur surface with chamfers therebetween to receive the femur component of a knee prosthesis. A tibial cutting guide is provided for preparing the proximal tibia that consists of a sleeve, with a tube telescoped therein, the ends thereof including pin arrangements for connecting them into the tibia, between the ankle and near the proximal tibia, an open tube end of the tibial cutting guide to receive a rod telescoped therein that mounts a cutting guide platform and includes a screw arrangement for releasably maintaining the rod and tube together. The cutting guide platform includes a body with a saw guide slot formed therethrough to receive a saw blade to cut across the proximal tibia to form a surface for accommodating a tibial component of the knee prosthesis, the cutting guide platform body further including an arrangement for securing it to the tibia, slightly below the proximal tibia, and a tibial resection guide for setting a depth of cut across the proximal tibia.

30 Claims, 5 Drawing Sheets

INSTRUMENTS FOR SHAPING DISTAL FEMORAL AND PROXIMAL TIBIAL SURFACES

BACKGROUND OF THE INVENTION

1. Field Of The Invention

The present invention relates to medical instruments and a method for their use and pertains particularly to an improved instrument system for accurately preparing and shaping distal femur and proximal tibia end surfaces to receive a knee prosthesis secured thereto.

2. Prior Art

In recent times knee surgery for the repair and/or replacement of knee joints has become increasingly common. Such total knee implant, when properly installed, will closely approximate or mimic natural knee movement. Even with such improvement in total knee structures, however, there still exists the problem of properly fitting and installing such prosthesis. Heretofore, with the surgical instruments available, a surgeon installing such implant must have had a high degree of skill in order to achieve optimum fit and alignment. It has therefore been recognized that it is desirable to provide an effective system of instruments and method for their use to insure a high degree of success in the preparation of the distal femur and proximal tibial ends to receive a prosthesis secured thereto.

Even prior to the present invention the need to provide such a system suitable for use by even a less skilled surgeon to reliably and efficiently prepare distal femur and proximal tibia ends for receiving a knee prosthesis has resulted in the development of several systems. One such system is shown in a patent by Petersen, U.S. Pat. No. 4,524,766 that involves a surgical knee alignment and cutting guide system and method. This system references a patient's mechanical axis and from that determination provides cutting guides for selective attachment for shaping the patient's proximal tibia to receive the tibia portion of the knee prosthesis and mounts cutting guides from the tibia components for appropriately shaping the distal femoral end to receive the femur portion of that knee prosthesis. Where the present invention is intended to accomplish the same result, the structure thereof and its use are decidedly distinct from this device. Particularly, for shaping the tibia proximal end, the present invention involves an elongate extensible support frame that, unlike the Petersen system, provides for a close calibration of length adjustment capability. Additionally, unlike this earlier Petersen patent that references from the tibia, the present invention references from the patient's distal femur and provides for locating the patient's mechanical axis from their anatomical axis, and after referencing that mechanical axis, employs an alignment guide and cutting guides that are distinct from those of the Petersen patent.

Another system for shaping the distal femur is shown in a patent by Lacey, U.S. Pat. No. 4,502,483. This patent, like the present invention, provides for locating a patient's mechanical axis relative to their anatomical axis and accordingly then locates and secures a femoral distal cutting guide to that bone end to form a first cut across the femoral condyle. From this first cut, the distal femur end is cut at a right angle to the patient's mechanical axis. Like the Lacey patent, the present invention references the patient's mechanical axis and provides for establishing a desired angle to their femur anatomical axis to calculate that mechanical axis. The cutting guides of Lacey, however, are structurally different from those taught by the present invention, and, of course, the Lacey patent does not involve a length adjustable tibial cutting guide as does the present invention.

The present invention provides a set of alignment and cutting guides and method for their use that is easier and more reliable for a surgeon to operate with as compared with earlier arrangements and provides a system that even a surgeon who has limited experience in total knee reconstruction surgery can use. The present invention provides a surgeon with the capability to simply and accurately prepare distal femur and proximal tibial bone ends to receive a preferred knee prosthesis fixed thereto within a time frame that is reasonable for the performance of the surgical procedure.

SUMMARY OF THE INVENTION

The principal object of the present invention is to provide an apparatus and system for accurately shaping distal femur and proximal tibia end surfaces to receive components of a knee joint prosthesis attached thereto such that the attached prosthesis will be aligned to function so as to approximate the functioning of a natural knee joint.

Another object of the present invention is to provide a system for determining a patient's mechanical axis with reference to their anatomical axis with an alignment guide of the invention that is arranged for fitting into a hole drilling into the distal femur end that intersects the femoral intramedullary channel, and further includes cutting guides that are sequentially attached to that alignment guide and shaped bone surfaces used in shaping that distal femur end to receive the femur portion of the knee prosthetic.

Still another object of the present invention is to provide a tibial cutting guide for attachment to a tibia between the patient's ankle and below their proximal tibial end, which guide is for alignment with the patient's mechanical axis and provides a cutting guide arrangement that is adjustable for controlling the depth of cut thereacross for forming the tibia proximal end to receive a tibia portion of the knee prosthesis.

Still another object of the present invention is to provide a system for accurately preparing the distal femur and proximal tibial ends such that the plane of each of said cuts across the bone ends will be appropriate to receive the portions of a knee prosthesis selected to reflect the spacing distance and size of the respective bone ends such that, the installed prosthesis will function as a total knee system, approximating the mechanical functioning of a normal knee.

In accordance with the above objects, the present invention is in a system of surgical instruments and a method for their use for preparing distal femur and proximal tibia ends to receive a knee prosthesis secured thereto that replace a natural knee. The distal femur end preparation portion of the system includes: a femoral alignment guide; anterior femoral cutting guide with locator; a distal femoral cutting guide; an A/P measuring guide; a femoral finishing guide; and the system for preparing the proximal tibia end includes; a tibial cutting guide with a cutting platform and a tibial depth resection guide. In practice, a surgeon, after opening the damaged knee area sequentially utilizes these instruments to prepare a patient's distal femur and proximal tibia ends to receive knee components of a select prosthesis secured thereto.

Use of the system of the present invention requires first a determination of the angle between a patient's anatomical axis and their mechanical axis to reproduce a use of the system of the present invention, which anatomical axis is determined by reference to the femur intramedullary channel. To verify this reference a hole is drilled into the distal femur that is parallel to the shaft of the femur to intersect the intramedullary channel. Whereafter the femoral alignment guide is secured to that distal femur surface so as to be perpendicular to the posterior femoral condyles. In such positioning, approximately equal amounts of medial and lateral femoral condyle are exposed posterior to or behind the guide. To the femoral alignment guide is attached an anterior femoral cutting guide that includes a locator that extends therefrom so as to just touch the interior cortex of that femur, proximal to the anterior condyles. So positioned, a saw or like cutting device is fitted through a cutting guide slot of that anterior femoral cutting guide and is reciprocated to cut across the femoral condyles. The depth of which cut is to be sufficient to accommodate the fitting a distal femoral cutting guide to that bone surface after removal of the anterior femoral cutting guide.

The distal femoral cutting guide is for pivotal mounting to the femoral alignment guide so as to be angularly adjustable thereto. The angular adjustability is around a transverse axis across the distal femur to position a cutting surface of the guide to a plane that is perpendicular to the patient's mechanical axis. The angular positioning, once set, is initially maintained by a pivot pin arrangement and is later secured by fitting two or three pins through appropriate openings in the guide that are turned into the femur. Thereafter, the femoral alignment guide can be left in place or removed as a saw blade is fitted through the slot in the distal femoral cutting guide and is reciprocated to cut across the face of the distal femur. This cut is thereby made across the distal femur end at a right or normal angle to the patient's mechanical axis. It is from this cut surface that the other cuts to be made in the distal femur are referenced.

After removal of the distal femoral cutting guide, and the femoral alignment guide, if such had been left in place, a measuring guide is fitted across that distal femur flat surface. The measuring guide includes spaced apart parallel feet on the bone engaging surface that are set on the cartilage of the posterior condyles and further includes a mobile gauge portion thereof that extends from the measuring guide body to rest on the cut anterior femoral surface. The measuring guide provides for sizing a femur portion of a knee prosthesis, which size can be read directly from a scale thereon. Thereafter, the measuring guide is removed and a femur finishing guide is fitted over that prepared flat femur distal end surface such that a top ledge adjacent to the bone engaging surface thereof will rest on the cut surface of the anterior femur. This guide, after careful fitting to the prepared distal femur, receives a drill fitted through holes formed therethrough that is turned into the bone end. To securely hold that finishing guide in place fasteners are turned into the drilled holes. So positioned, a reciprocating saw blade, or like cutting instrument, can be fitted through appropriate slots formed in that femur finishing guide to cut, in turn, the femur posterior condyles, posterior chamfers, anterior condyles and anterior chamfers. The posterior and anterior distal femur sides are thereby cut parallel to one another, each having an equal angular chamfer that extends from the parallel surfaces and intersects the distal femur end. The distal femur end is thereby equaled or squared off to receive a femur portion of the select knee prosthesis fitted thereto.

With the distal femur end prepared, as set out above, the opposing proximal tibia end is shaped to compliment that distal femur end preparation utilizing a tibial cutting guide. The tibial cutting guide of the present invention is arranged for attachment to the tibia to extend between the center of the patient's ankle and proximal to the tibial tubercle. The tibial cutting guide is set to be parallel to the tibia mechanical axis and is constructed to be telescoped between its two tibia connection points. The tibial cutting guide additionally involves a cutting platform that is arranged to be independently telescoped and includes a cutting guide slot formed thereacross that is to receive a reciprocating saw blade fitted therethrough to cut across the tibia. The plane of which tibia cut, to accommodate the selected tibia prosthesis component, is at a ten degree (10°) angle below a perpendicular plane to that patient's mechanical axis. The cutting platform further includes a tibial depth resection guide that is positionable across the proximal tibia end to set a desired depth of tibial resection. Appropriately setting the depth of cut enables the surgeon to compensate for bone defects in that proximal tibial surface.

The above sets out the apparatus and system of the present invention for preparing the distal femur and proximal tibia ends. To fully prepare a patient's knee to receive a knee prosthesis additionally involves preparing their patella to receive a certain thickness of patella component of that knee prosthesis secured thereto. Patella preparation in the system of the present invention preferably involves well known tools and a system for the use for longitudinally cutting the patella at the level of the quadriceps tendon and preparing it to receive a selected patellar implant.

With the distal femur and proximal tibia ends appropriately formed, as set out above, and after the preparation of the patella, a trial reduction and fixation of the knee prosthesis is attempted. This trial involves fitting the prosthesis components to the prepared surfaces and checking the patient's range of motion and the ligament stability that will be afforded by the prosthesis attachment. This check may include performing necessary tissue release to effect the desired range of motion. After that trial, the proximal tibial end is preferably first fitted with the tibial base plate followed by fitting the femur portion of the prosthesis to the prepared distal femur end and securing the patella prosthesis to the patella. The result is tested and thereafter the incision into the kneecap is appropriately closed and dressed.

The above sets out a brief summary of the components of the system along with their use in preparing the opposing distal femur and proximal tibial ends and the patella to receive a selected knee prosthesis fitted thereto that will, after healing, mimic or approximate the range of motion of a natural knee.

THE DRAWINGS

These and other objects will be apparent from the following detailed description in which preferred embodiment and method for its use of the present invention has been described in detail in conjunction with the accompanying drawings.

DETAILED DESCRIPTION

Rational and Pre-Operative Planning

The present invention is in a system of the instruments and a procedure for their use for performing a total knee arthroplasty. The success of this procedure is directly dependent on the re-establishment to the patient of a normal lower extremity alignment, proper component design and orientation, secure component fixation, and adequate soft tissue stability. The present invention and the system for its use has been developed to satisfy these objectives.

The present invention is in a system of instruments for use by a surgeon to provide for a restoration of normal lower extremity alignment of knee prosthesis components that are aligned relative to the patient's mechanical axis. The patient's mechanical axis is established by drawing a line on an appropriate x-ray from the patient's hip to ankle when the patient is in a stable, erect attitude. In practice, this mechanical axis is generally a line or axis drawn through the longitudinal center of the patient's tibia that intersects the center of the femur head. This axis must be measured for each particular patient, and, for the purposes of this invention, is generally then referenced from the patient's anatomic axis, which is the axis through an intramedullary channel in the femur bone. This angular difference from the vertical of the mechanical to anatomic axis has been found in practice to be usually five degrees (5°) and, in a few women it has been found to be six degrees (6°). Occasionally, in patients who have had total hip arthroplasty with a femoral component that has more valgus in the shaft angle then usual, or in the patient with coxa valga, this angular difference will be four degrees (4°) or even three degrees (3°). In a very rare patient who has significant coxa valga or a broad pelvis with a long femoral neck the angular difference may be seven degrees (7°) or eight degrees (8°). Accordingly, the present invention provides for sitting a range of angles of a cutting guide relative to the anatomic axis, as will be discussed later herein, between zero degrees (0°) and eight degrees (8°).

Figures 1, 2, 3, 4:
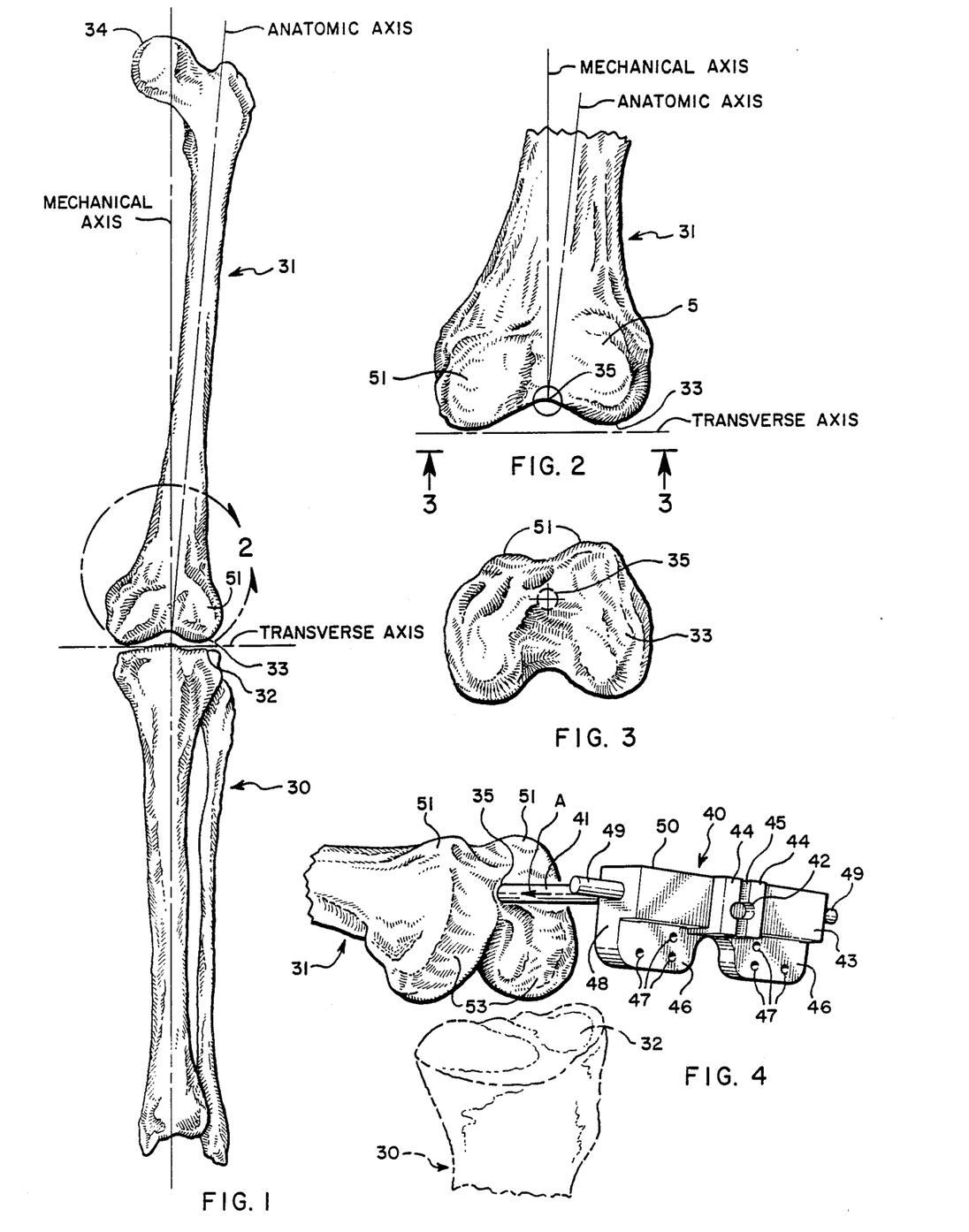
FIG. 1 is a view of a femur and tibia bones of a human leg showing, with broken lines, the patient's anatomic and mechanical axes.
FIG. 2 is a sectional taken within the line 2 of FIG. 1 showing an expanded view of the distal femur end, with the respective anatomic and mechanical axes defined in broken lines.
FIG. 3 is an end sectional view taken along the line 3—3 of FIG. 2 showing in broken lines the position of a hole to be drilled therein to intersect the femur intramedullary channel.
FIG. 4 is a profile perspective view and a femoral alignment guide that includes an intramedullary rod aligned for fitting into the hole shown located in broken lines in FIG. 3 and shows in broken lines the proximal tibia end with the patient's leg bent at the knee.

With the angular difference between the patient's mechanical and anatomical axis, in a normal patient their femur channel, that is also known as the intramedullary channel, will duplicate their anatomic axis. A most accurate method of femoral component alignment is therefore provided by using that intramedullary channel as a reference. In this procedure, a pre-operative x-ray film is first taken with an intramedullary rod installed therein to clearly show the channel. In the pre-operative planning, the x-ray is preferably a standing radiograph made showing the center of the femoral head, the knee and as much as the tibia as possible, preferably to include the ankle. Alternatively, a single A/P radiograph of the entire femur will allow for correct calculation. On the developed radiograph, as illustrated in FIG. 1, a line is drawn from the center of the femoral head to the center of the distal femur at the knee with a second line drawn down the middle of the distal femoral shaft in the area where an intramedullary alignment rod is fitted to reproduce the anatomic axis of the femur. The angle between these two lines is the angle that is reproduced during surgery using the instruments of the present invention.

The above sets out a preferred practice for determining the patient's mechanical axis in relation to their anatomic axis. Once the anatomic axis is established, the amount of distal femur removal can be calculated, providing for cutting that bone end to form a plane surface that is perpendicular to the mechanical axis using the system of the present invention as set hereinbelow. In the vein of locating the patient's mechanical axis and therefrom making perpendicular cuts across the distal femur and proximal tibia, for a preferred Miller/Galante tibial component the proximal tibia is to be cut at an angle of ten degrees (10°) to a plane perpendicular to that mechanical axis. To prepare the proximal tibia, the present invention utilizes a guide that is used independently from the distal femur preparation instrument and is fitted and secured between the center of the upper tibia and the ankle. This guide, once installed, provides a cutting guide platform for cutting across the proximal tibia at the desired angle of ten degrees (10°) below a plane that is perpendicular to the patient's mechanical axis.

FIG. 1, as set out above, illustrates the relationship between a patient's femur and tibia bones as would be shown in an A/P radiograph, therein the tibia is shown at 30 and the femur is shown at 31. FIG. 1 identifies the patient's mechanical and anatomic axis and a transverse axis that is perpendicular to the mechanical axis of the respective opposing faces identified at 33 and 32 of the distal femur and proximal tibia. The mechanical axis is shown as a line drawn from approximately the center of the distal femur end to the femur head 34. In FIG. 1 therefore the angle between the mechanical axis and the anatomic is established by measuring the angle difference of the two axis as shown in the x-ray, which angle, as set out above, is usually five degrees (5°) or six degrees (6°). FIG. 2 is an expanded sectional view taken within the line 2—2 of FIG. 1 that shows the distal femur 33 with the mechanical and anatomic axis converging at a point 35. The convergent point 35, as illustrated also in FIG. 3, is the point on the bone end that will be immediately opposite to and on line with the femur intramedullary channel and is therefore the point where an end of a drill is positioned to drill into the bone to intersect that channel. After locating this point 35 a surgeon drills a hole into the distal femur that intersects and enters that intramedullary channel. The hole formed at 35 should have an appropriate diameter to receive an intramedullary rod 41 portion of an femoral intramedullary alignment guide 40, shown in FIG. 4, whose function will be described in detail hereinbelow.

The above sets out the procedure for determining and utilizing a patient's anatomic axis as a reference for sequentially attaching cutting guide components for surgically shaping the distal femur end to receive a femur component of a Miller/Galante prosthesis. No calculations are necessary to provide for locating the mechanical axis of the proximal tibia, as the patient's mechanical axis is defined visually as the longitudinal center of the tibia and a tibial cutting guide is to be secured between the proximal tibia and the center of the ankle. The tibia cutting guide is secured in the tibia at the two points and mounts a cutting platform to extend from the end thereof closest to the proximal tibia to provide a guide arrangement for receiving a saw to cut that proximal tibia thereacross.

Surgical Approach

In a practice of the system of the present invention for preparing a patient's knee to receive the components of a knee prosthesis, a standard medial parapatellar arthrotomy is first made through a slightly curved or direct anterior skin incision at the knee area. If it is anticipated that a lateral retinacular release will be necessary this is done at this time. Thereafter, the patella is everted and the knee is flexed and is maintained in that flexed attitude. The soft tissue of the suprapatellar pouch proximal to the cartilage surface is then removed so as to expose the distal femur. If a significant pre-operative soft tissue contracture exists, a preliminary soft tissue release can be made at this time to facilitate exposure of the distal femur and proximal tibia, which release also lessens the amount of soft tissue release that will be needed later. The femur and tibia ends are prepared independently and either one can be prepared first. However, in practice the distal femur is routinely prepared first as the resection of the posterior femoral condyles will offer greater exposure of the proximal tibia, thereby facilitating its preparation.

The Surgical Procedure

With the patient's knee opened appropriately and flexed, as illustrated in FIG. 4, the site or location for inserting a femoral alignment guide 40 is selected on the distal femur. This location is shown in FIG. 3 as a hole 35 that is drilled into the distal femur. Hole 35 will be anterior to the intercondylar notch in that distal femur. In the drilling process, approximately an eight millimeter hole is preferably formed into that bone mass. In that hole formation it is important that this hole be parallel to the shaft of the femur in both the A/P and lateral projections. In practice, only the cancellous bone of that distal femur needs to be drilled as the femur hollow diaphysis will provide no resistance to the insertion of the intramedullary rod. The drilled hole, it should be understood, is important only for alignment and is not for component positioning on that distal femur.

Shown in FIG. 4, a femoral intramedullary alignment guide 40, hereinafter referred to as alignment guide 40, is shown as including an intramedullary rod 41 that extends from from a bottom or undersurface 52, the direction of insertion shown with an arrow A, as being in the intramedullary channel through hole 35. The intramedullary rod 41 extends at a right or normal angle from the alignment guide undersurface and is intended to be replaceable to be turned or screwed therein and comes in various lengths appropriate for the particular patient and procedure being performed. In practice, an intramedullary rod 41 length of nine inches is generally adequate for an accurate reproduction of the patient's anatomical axis. However, to compensate for problems as may exist with the femoral anatomy, such as where it has been altered as in a femur with a long stemmed total hip femoral component or with a femoral fracture malunion, then an intramedullary rod of four inches in length is provided. It is, of course, preferable to use the longest intramedullary rod 41 possible so as to guarantee a most accurate replication of the patient's anatomical axis.

In the installation of the intramedullary alignment guide 40, as shown in FIG. 4, a handle, not shown, is preferably turned into a central threaded opening 42 formed into the upper surface or face 43, of the alignment guide 40. Opening 42 is formed through a ridge 44 that includes a lateral slot 45 that extends across the ridge face, the function of which slot 45 will be discussed in detail hereinbelow. The ridge 44 and slot 45 project outwardly from the face 43 that, in turn is stepped downwardly into toes 46 that are separated at the alignment guide center, that is intersected by slot 45. The toes 46 are shown to include holes 47 formed therein that are for receiving fasteners, as will be discussed hereinbelow. The alignment guide 40 opposite ends 48 includes posts 49 that extend outwardly and oppositely to serve as pivot rods for receiving a yoke-type tool thereover, not shown, as needed for manipulating the alignment guide 40.

Figures 5, 6, 7, 8:
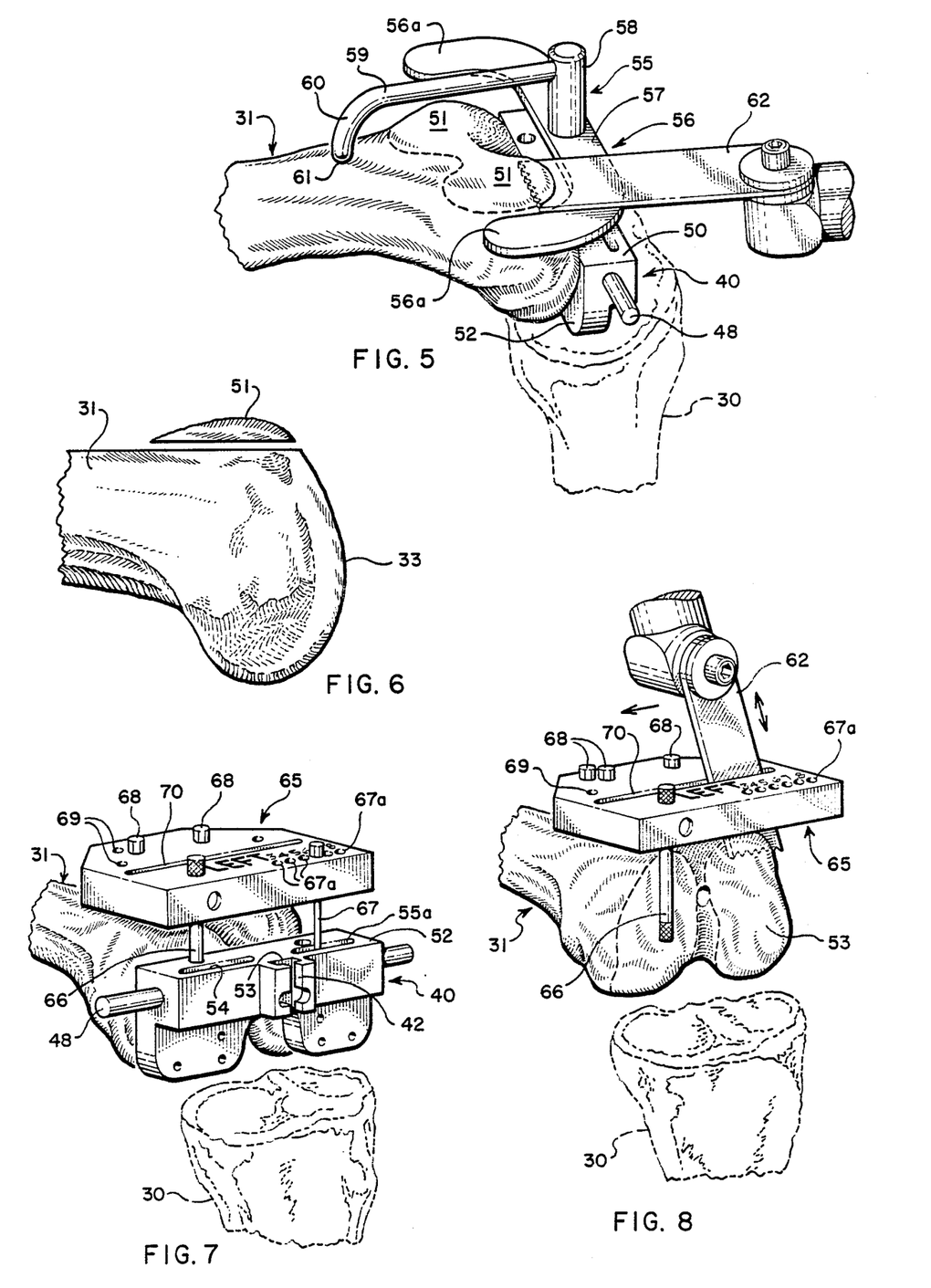
FIG. 5 shows the femoral alignment guide of FIG. 4 installed in the femur, whereto a femoral cutting guide is attached that is shown to include a U-shape platform, the legs thereof extending from that femoral alignment guide, and includes a locator to contact the anterior cortex and shows a saw blade resting on that anterior femoral cutting guide platform that is reciprocated to cut the anterior femoral condyles from the distal femur.
FIG. 6 is a profile view of the femur distal end showing the anterior femoral condyles separated therefrom.
FIG. 7 shows a distal femoral cutting guide that has been fitted to the femoral alignment guide that is shown resting on the flat surface of the distal femoral end that was formed by the removal of the femoral condyles, as shown in FIG. 6, the distal femoral cutting guide shown secured to the alignment guide by fitting a pin through a selected hole, one of a number of holes that are identified with ascending numbers from 3 to 8 which numbers represent angles from a right angle that is the angular difference between the patient'W's anatomic and mechanical axes.
FIG. 8 shows the distal femur end after the femoral alignment guide of FIG. 7 has been removed, and shows a saw blade fitted through a slot in the femoral distal cutting guide, the distal femur end shown being cut thereacross to leave a flat transverse surface that is perpendicular to the femur mechanical axis.

In practice, with the universal handle, not shown, turned into the hole 42, provides a point for gripping by a surgeon who, by pivoting the alignment guide 40 appropriately back and forth can slide the intramedullary rod 41 through hole 35 and into the femur intramedullary channel. During this installation, it is important to control rotation of the alignment guide as it approaches the articular surface of the distal femur, which final positioning can be effected by controlling tool pivoting at posts 49. The proper orientation of the alignment guide 40 is such that a flat top or cutting surface 50 therof that is an upper flat longitudinal end of that alignment guide, shown best in FIG. 5, is parallel to the posterior femoral condyles 51, as shown in FIGS. 1 through 6. A surgeon will know when the alignment guide 40 is correctly placed when equal amount of medial and lateral femoral condyles are exposed posterior to the guide. When equal amounts of both condyles are so exposed, the alignment guide intramedullary rod 41 can be forced or driven into the femur channel until an alignment guide undersurface 52, illustrated in FIG. 5, contacts the distal femur 33, as shown in FIG. 4. If sections or portions of the distal femur surface are not formed or are missing as from injury or disease, then adjustments need to be made to the alignment guide 40 placement to verify that the cutting surface 50 will be parallel to a plane through the condyles. So positioned, a fixation pin, not shown, that extends outwardly at a normal angle form the underside 52 of the alignment guide 40 will be turned to engage the sub-condyle bone or distal femur end so as to prevent rotation. Additionally, pins can be fitted through holes 47 in the respective toe portions 46 of the alignment guide 40 that are turned or driven into the lateral femoral condyle. The intramedullary alignment guide 40 is thereby fixed to the lateral femoral condyle portion of the distal femur end.

With alignment guide 40 installed, as set out above, an anterior femoral cutting guide 55 can be attached thereto. The anterior femoral cutting guide, shown in FIG. 5, includes a slide or shoe located on the undersurface thereof that is arranged to fit within and travel along the slot 45 of ridge 44 of the intramedullary alignment guide 40. As shown best in FIG. 7, the slot 42 is internally stepped outwardly to have a greater width in a channel portion 53 than at the intersection of slot 45 with the surface of ridge 44, shown in FIG. 4. So arranged, the slide or shoe, not shown, of the anterior femoral cutting guide 55, having dimensions that are similar to but slightly less than the channel portion 53, is fitted into that channel portion to travel therealong, as shown in FIG. 5. Such shoe travel brings the undersurface of a yoke portion 56 of that anterior femoral cutting guide into engagement with the cutting surface 50 of the intramedullary alignment guide 40. Yoke 56, as shown best in FIG. 5, has a U shape with equal legs 56a and 56b with a web 57 therebetween and further includes a mast 58, that is centrally fitted to the yoke web 57, to extend at a normal angle upwardly therefrom. The mast 58 includes an arm 59 that extends at a normal angle therefrom and is in a plane that is essentially parallel to the plane of the co-planar yoke legs 56a and 56b, that are, in turn, essentially parallel to the femur intramedullary channel. The arm 59 is curved at its end into a hook 60 that terminates in a flat end surface 61 that essentially is in the plane of the yoke legs 56a and 56b. Flat end surface 61 is for contacting the femur at a point beyond the anterior cortex from the distal femur, just proximal to the anterior condyles 51, setting a depth of cut made by operation of a saw blade 62, as shown in FIG. 5, resting on yoke 56. With the anterior femoral cutting guide 55 so installed, the yoke legs 56a and arm 59 will be parallel to the femur intramedullary channel and are essentially perpendicular to the cutting surface 52 of the alignment guide 40. As set out above, as illustrated in FIG. 5, the yoke 56 upper surface serves as a rest for supporting saw blade 62 thereon. Which saw blade is part of a reciprocating saw arrangement that is operated to cut through the anterior condyles 51. After which, as shown in FIG. 6, the bone segments are removed. The cut is made flush with the anterior cortex of the femur to reduce the possibility of notching the anterior surface of the femoral cortex. This cut or resection will be essentially parallel to the intramedullary channel which is, as set out above, the patient's anatomic axis. After the anterior condyles 51 are removed, the anterior femoral cutting guide 55 is removed from its engagement with the alignment guide 40 by sliding the shoe portion thereof, not shown, out from the channel portion 53, the shoe traveling along the slot 45 until it exits that slot.

As set out above, the alignment guide 40 is to remain in position after the anterior femoral cutting guide 55 has been removed. It is then used as a platform for mounting a distal femoral cutting guide 65, as shown in FIGS. 7 and 8. The distal femoral cutting guide 65 is for cutting across the distal femur end so as to provide a flattened bone end surface which surface is to be perpendicular to the patient's mechanical axis. This cut is made based on a determination of the relative angular displacement of the patient's mechanical axis from their anatomic axis which determination is made as described hereinabove. To make this cut, the distal femoral cutting guide 65 is fitted to the alignment guide 40 such that a cutting slot 70 thereof will be displaced relative to the undersurface 52 of the intramedullary alignment guide 40, the angular difference between the patient's anatomic and mechanical axes. So arranged, as shown in FIG. 8, cutting slot 70 will be exactly perpendicular to the patient's mechanical axis to accommodate blade 62 fitted therethrough.

Shown in FIG. 7, the distal femoral cutting guide 65 is secured to the alignment guide 40 by fitting a pivot pin 66 into a cavity 54 in the alignment guide 40 cutting surface 52. This pivot pin is fitted so as to allow the distal femoral cutting guide 65 to pivot slightly with respect to that intramedullary alignment guide 40. To set the particular angular displacement, an alignment pin 67 of the distal femoral cutting guide 65 is provided for fitting through one of the holes 67a that are formed through the cutting guide and are labeled three (3) to eight (8). Each number represents an angle and holes 67a are thereby each offset by one degree from adjacent holes. As shown in FIG. 7, the pin 67 will travel through a selected hole 67a and into a pin slot 55a located in the cutting surface 52 of the alignment guide 40. The slot 55a is appropriately ridged, or the like, to receive the pin 67 end turned therein to provide for setting and locking an angular displacement between the mechanical and anatomic axes. FIG. 7 shows the pin 67 fitted through a hole 67a identified as hole 6. This hole selection reflects a six degree (6°) angle offset from a perpendicular to the intramedullary alignment guide 40 cutting surface 52. The pin 67 turned into the slot 55a and the pivot pin 65 fitted into cavity 54 effects two points of coupling to join the units together as shown in FIG. 7. So arranged, the distal femoral cutting guide 65 positioning is maintained to the alignment guide 40. Additionally, as required to maintain the components together, additional pins 68, shown in FIG. 7, can be fitted through openings 69 in a flat anterior portion of the distal femoral cutting guide 65, which pins 68 are turned into the flattened portion of the femur that was produced with the removal of the anterior condyles 51.

Shown in FIGS. 7 and 8, the distal femoral cutting guide 65 includes a flat undersurface that is to rest on the flat surface created by the removal of the anterior condyles 51. Distal femoral cutting guide 65 placement is determined by whether the bone being cut is a right or left femur. To confirm proper alignment after removal of the alignment guide 40, as illustrated best in FIG. 8, a rod can be inserted through hole 35 and up the intramedullary channel until that rod tip is proximal to the femoral head. This rod placement can be checked by means of an x-ray or A/P radiograph to verify that the distal femoral cutting guide is properly positioned at the angle to the anatomic axis whereby the distal femur will be cut perpendicular to the patient's mechanical axis.

Figure 9:
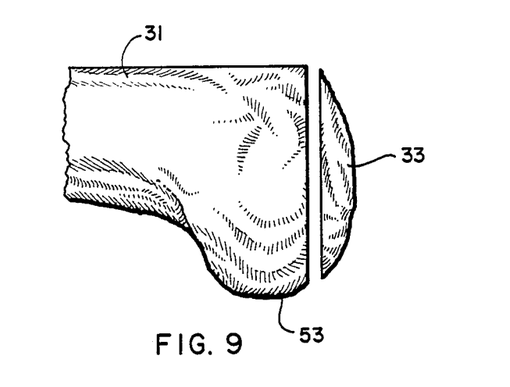
FIG. 9 shows the distal femur end having a portion of the distal femur end separated therefrom.

With the distal femoral cutting guide 65 positioned, as set out above, the alignment guide 40 and intramedullary rod 41 can be removed or left in place, at the surgeon's option, while the distal femur end is cut. The advantage of leaving the alignment guide 40 and intramedullary rod 41 in place is that additional stability is provided. However, if the alignment guide is left in place then the surgeon will have to cut around the intramedullary rod 41 in the distal femur end shaping process. FIG. 8 shows the alignment guide 40 as having been removed and shows the pivot pin 66 extending therefrom. So arranged, the alignment pin 67 is shown removed and to maintain the proper distal femoral cutting guide positioning, three sharp pins 68 are shown fitted through holes 69 in the anterior portion of the that distal femoral cutting guide and travel into the femur. So arranged, saw blade 62, that is like the saw blades described hereinabove, is inserted through a cutting slot 70 that is formed through the distal femoral cutting guide. The saw blade 62 is then reciprocated appropriately to cut through the distal femur end, as illustrated best in FIG. 9. This cut, as set out above, will be perpendicular to the patient's mechanical axis and is made at a depth to the resection or cut an amount of bone as will be replaced by the thickness of a femoral component of the knee prosthesis. The thickness of bone resection is controlled by having the alignment guide 40 flush against both the medial and lateral condyles, which positioning is maintained after the alignment guide 40 is removed by pins 68 fitted through openings 69. The prepared surface is then checked for flatness and, if necessary, is further shaped to insure that the surface is completely flat. Verifying that the surface is completely flat is extremely important as this surface is the reference for subsequent cutting guide attachment and must therefore be flat to insure a proper fit of the implant.

The distal femur end surface, prepared as set out above, provides a flat surface wherefrom the other cuts or resections of the distal femur are made. In complex cases, such as where a significant flexion contracture has occurred, it may be necessary to cut additional bone from the distal femur end. In such case, after the standard distal femoral cut has been made, as set out above, the pins 68 are removed and the distal femoral cutting guide 65 is reconnected to the alignment guide 40 that is repositioned by progressive insertion of the alignment guide rod 41 further into the femur intramedullary channel to a point that is slightly more proximal When the desired positioning is achieved, then the distal femoral cutting the guide 65 is again pinned, as shown in FIGS. 7 and 8, and additional bone is resectioned or cut therefrom, as described above. It is uncommon that a second resection of the distal femur end will be required. Such is, however, possible and may be found to be necessary after the prosthesis components have been provisionally installed for trial reduction and/or where ligament tightness and extension is found to be excessive. Such problems would be an indication of a need for slightly more distal femoral resection.

Figure 10:
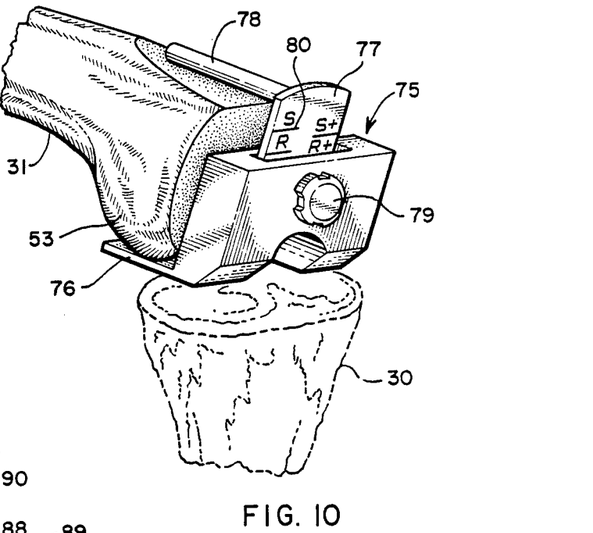
FIG. 10 is a profile perspective view of measuring guide that has been fitted onto the distal femur end as shown prepared in FIG. 9, showing the feet of that measuring guide resting on the cartilage of the posterior condyles with a mobile gauge portion thereof shown resting on the cut anterior femoral surface, that mobile gauge shown to preferably include calibrations thereon for use in selecting a proper size of a femur portion of a knee prosthesis for attachment thereto.

For determining the anteroprosterior size of the prepared distal femur end such that a correct size of a femur component or portion can be selected for use, the invention provides a femoral A/P measuring guide 75. The femoral A/P measuring guide 75 is shown in FIG. 10 and is for fitting to that prepared distal femur surface. In that fitting process the femoral A/P measuring guide 75, hereinafter referred to as measuring guide 75, is first placed flat onto the smoothly cut distal femur end, with feet 76 thereof resting on the cartilage of the posterior condyles 53. So arranged, an arm 78 of a mobile gauge 77 of that measuring guide is moved into engagement with the flat anterior femoral surface that has been prepared as illustrated in FIG. 6. A mobile gauge 77 of the measuring guide 75 can then be tightened in place by turning a screw head 79 with an appropriate tool, not shown, which turning brings the screw end into binding engagement with the surface of that mobile gauge 77 within the measuring guide 75. The mobile gauge is thereby maintained in an attitude like that shown in FIG. 10. So arranged, the proper femoral component size can be read off from a scale 80 of the mobile gauge 77 or the size can be read off the mobile gauge while the measuring guide 75 is in place without turning of screw head 79. The scale 80 includes equally spaced calibrations that preferably correspond to six sizes of femoral components: small; small plus; regular; regular plus; large; and large plus. If the reading is between two sizes, a smaller size of femoral component is to be chosen. Choosing the smaller size will prevent excessive ligament tightness flexion. After component selection, the measuring gauge 75 is removed and, as needed, screw head 79 is turned to release mobile gauge 77.

Figure 11:
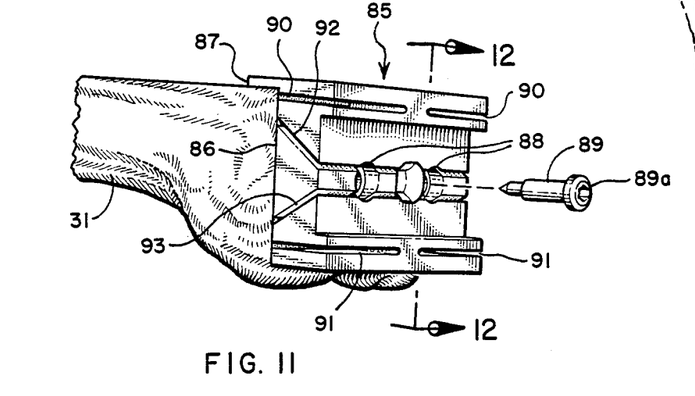
FIG. 11 is a profile perspective view of the distal femur end shown fitted with a femoral finishing guide with a pin shown aligned to turn into a hole for holding that guide to the prepared flat distal femur end.
Figures 12, 13:
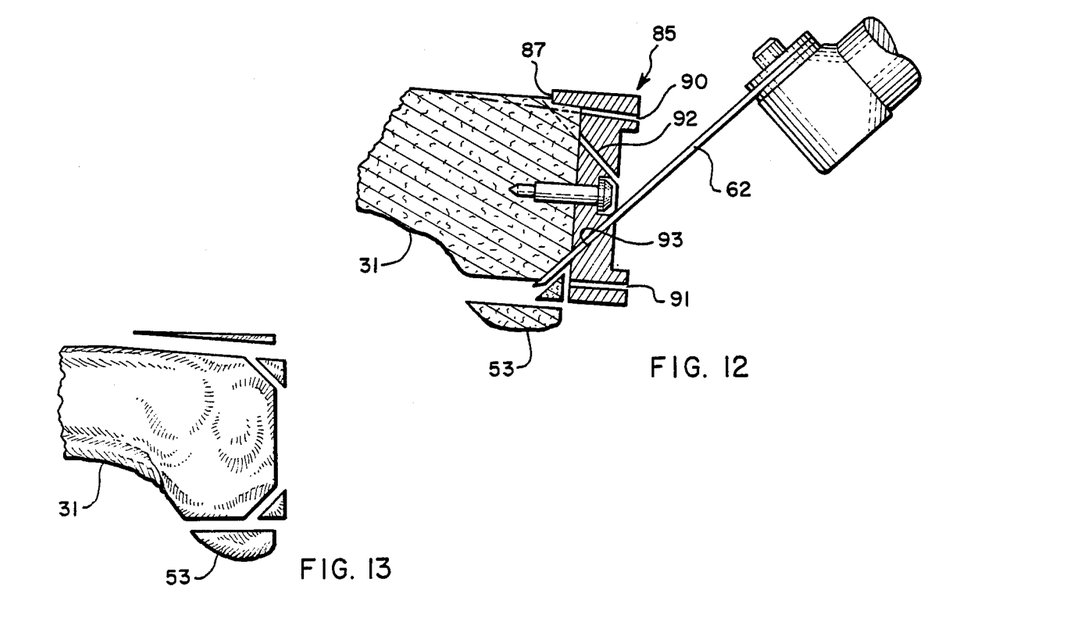
FIG. 12 is a cross-sectional view taken along the line 12—12 of FIG. 11, the femoral finishing guide as including guide slots with a saw blade shown fitted through one guide slot.
FIG. 13 shows the femur distal end having bone portions separated therefrom.

As a final distal femur preparation tool the invention provides a femoral finishing guide 85, as shown in FIGS. 11 and 12. A correct size of femoral finishing guide is selected based on the reading on mobile gauge 77 of the measuring guide 75, as discussed above. From that measurement, a preferred size of femoral finishing guide is selected for the particular size of femur component or portion of the knee prosthesis. The femoral finishing guide 85 is attached, as shown in FIG. 11 and in the sectional view of FIG. 12, to the prepared end surface of the distal femur and includes a flat underface 86 that will fit closely over that prepared distal femur end. For positioning, the femoral finishing guide includes a ledge 87 that extends at a right angle outwardly from the undersurface 86 for positioning to overlap the edge of the resectioned or cut surface of the anterior femur. This ledge 87 placement deters rotation of the instrument, which instrument must be centered mediolaterally on that distal femur end. When so centered, a bolt is temporality turned through a center hole of the finishing guide, as shown in FIG. 11, to hold the finishing guide in place. A drill, not shown, is then fitted through each of the peg holes 88 on either side of the hole and is turned into the distal femur. Holding pegs 89 are then turned into the formed holes, each peg expanded to lock therein. Thereafter, the bolt is removed and the center hole drilled and filled with another peg 89, as shown in FIG. 12. In holding peg placement, it is preferred that each holding peg 89 be installed such that the head 89a will be below the level of certain chamfer cutting slots 92 and 93 whose function is explained herein below. In the peg setting process, a peg turning device, not shown, can be used to countersink the pegs to below the level of the cutting slots.

The femoral finish guide 85, installed as set out above, provides respectively, anterior and posterior condyle cutting slots 90 and 91, and chamfer cutting slots 92 and 93. The respective slots, as shown in FIG. 12, are each for receiving a reciprocating saw blade 62 fitted therethrough to cut or resection portions of the distal femur, as illustrated in FIG. 13. In practice, it is preferred to first cut or resection the posterior condyle at cutting slot 91, followed by cutting or resectioning the posterior chamfers at cutting slot 93. Thereafter, the anterior condyles are further cut or resectioned at cutting slot 90 to square that surface to a right angle to the distal femur end surface, followed by cutting or resectioning the anterior chamfers at cutting slot 92. These cuts or resections are illustrated in FIG. 13 and complete the femur distal preparation. Preferably, to maintain optimal stability of the femoral finishing guide during the bone resection, the cuts or resections are performed in the above set out order, but can, of course, be made in another order within the scope of this disclosure.

The above set out components of the invention and their use provide for the preparation of a patient's distal femur to receive a femur component or portion of a knee prosthesis. In practice, a femur component manufactured by Miller/Galante Knee System is preferred for installation to the prepared bone end. To compliment the preferred femoral component, the present invention employs preferred Miller/Galante tibial component. The preferred Miller/Galante prosthesis is manufactured by Zimmer, Inc. of Warsaw, Indiana with the tibial component at ten degrees (10°) of posterior slope to the mechanical axis of the tibia. Therefore, where, as set out above, the patient's distal femur is prepared to provide a flat surface that is exactly perpendicular to the patient's mechanical axis, the proximal tibia is prepared to have a ten degree (10°) slope from and below a plane that is perpendicular to that mechanical axis to accommodate te preferred tibial component. To accurately provide this cutting or resectioning, the present invention provides a tibial cutting guide 100, shown in FIGS. 14 and 15. In practice, in a utilization of this tibial cutting guide, it is important to start the cut medially at the proximal tibia, the slope to be from the posterolateral corner to the posterior cortex to insure that the surface will not be canted relative to that patient's mechanical axis and will at a consistent ten degrees (10°) thereacross.

Figures 14, 15, 15A:
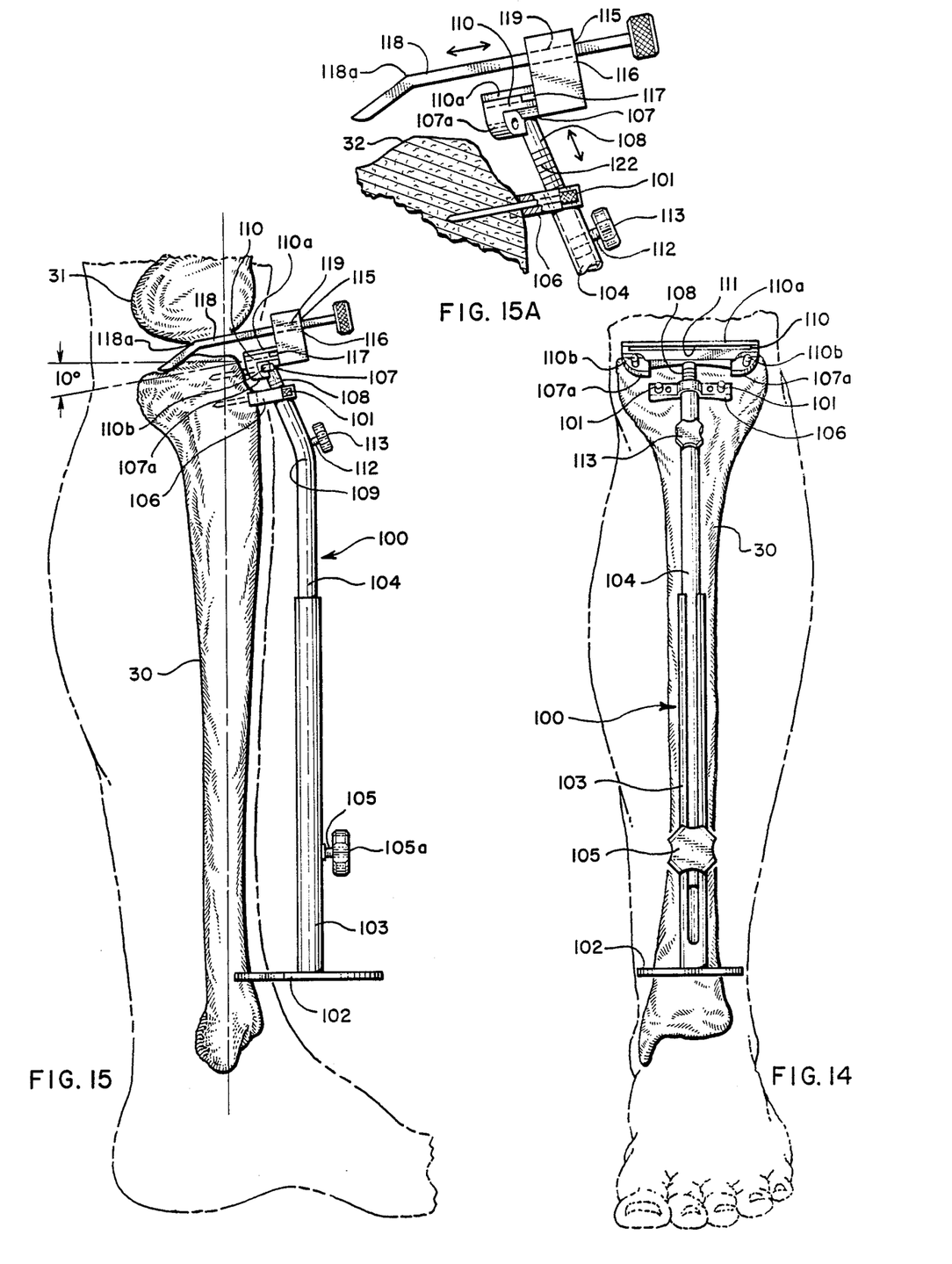
FIG. 14 is a front elevation view of a patient's lower leg from knee to foot, showing a tibia cutting guide attached at points at their ankle and proximal to the tibia tubercle, the tibia cutting guide shown as including a cutting platform for positioning relative to the proximal tibia such that a saw guide slot portion thereof will be positioned to receive a saw blade therethrough to cut across that proximal tibia.
FIG. 15 shows a side elevation view the of the tibial cutting guide of FIG. 14, with the cutting platform thereof and includes a tibial depth resection guide with an arm for extending across the proximal tibia end to set a desired thickness of the proximal tibia end section to be cut.
FIG. 15A shows an enlarged view of the end of the tibial cutting guide secured at one end to the tibial tubercle with the cutting platform telescoped therefrom and the tibial depth resection guide fitted thereto.

Shown in FIGS. 14 and 15, the tibial cutting guide 100 is preferably positioned between the ankle and a point on the upper tibia that is close to the proximal tibia, and is centered laterally between these two points. To secure the tibial cutting guide, as illustrated best in FIG. 15, the guide end closest to the proximal tibia is secured to the bone with pins 101 that are inserted in holes formed in the ends of a strap 106 that is secured to a telescoping tube 104. The opposite or ankle end of the tibial cutting guide includes a spike end 102 that is driven into the tibia, approximately at the ankle. The tibial cutting guide 100 includes the tube 104 that, as set out above, is connected to the tibia close to the proximal tibia, and is telescoped into an end of a sleeve 103 that is secured, on its other end, to spike end 102, extending perpendicular therefrom. By selectively telescoping the tube 104 into the sleeve 103 provides for a length adjustment capability to the tibial cutting guide 100. To lock the telescoping tube 104 in sleeve 103, a bolt 105 is provided that is turned into the telescoping tube shortening the distance between the undersurface of the head 105a thereof to the sleeve 103, providing for locking the sleeve and telescoping tube together. To facilitate turning of the bolt 105, the head end 105a, as shown in FIGS. 14 and 15, is large to accommodate manual turning. A surgeon can thereby fix the tibial cutting guide end at strap 106 to the tibia and thereafter telescope the tube 104 into or out of the sleeve 103 along the tibia for optimumly locating a point at the patient's ankle for inserting the spike end 102.

Shown in FIG. 14, to facilitate securing the tibial cutting guide 100 end proximate to the proximal tibia, includes the strap 106 that is secured to extend across the bone end and has holes therein that receive pins 101 fitted therethrough and turned into the proximal tibia. The strap 106 thereby spans the telescoping tube 104 end and provides at least two points of coupling of that tibial cutting guide end to the tibia. The opposite tibial cutting guide end is maintained to the ankle spike end 102, providing, thereby, a connection arrangement that is very stable and secure and limits a likelihood of rotation of the tibial cutting guide after its installation.

Shown in both FIGS. 14 and 15 and the enlarged sectional view of FIG. 15A, the tibial cutting guide includes a cutting platform 107. The cutting platform 107 is secured to the end of a rod 108 that is, in turn, telescoped into the telescoping tube 104 to move freely back and forth as illustrated by a double headed arrow. The sliding of rod 108 in the telescoping tube 104 provides a capability for setting an exact cutting platform 107 positioning after the sleeve 103 and tube 104 are releasably connected together and with the assembly is fixed to the tibia, as set out above. For aligning the cutting platform 107, that is shown as a block that is shown to be essentially rectangular with a flat undersurface and includes downwardly projecting tabs 107a that extend therefrom away from the proximal tibia and perpendicularly to a cutting slot 110 that is formed laterally therethrough. The slot 110 is for guiding a saw blade, not shown, fitted therethrough. The telescoping tube 104, shown best in FIG. 15, is preferably bent at 109, the rod 108 end thereby prohibited from further telescoping travel therein on contact with this bend. The bend 109 angles rod 108 to angle the cutting platform 107 and slot 110 therein to approximately ten degrees (10°) below a plane perpendicular to the tibia mechanical axis, as shown in FIG. 15. The cutting platform rod 108 is thereby free to slide back and forth within the telescoping tube 104 moving the slot 110 of the cutting platform vertically to set a desired thickness of bone to be removed from across the proximal tibia. Once the desired depth of cut is established, a bolt 112, as shown in FIGS. 14, 15, and 15A, that is threaded at one end and has an opposite broad head end 113 for manual turning, is turned through an appropriate threaded opening or hole formed through the telescoping tube 104, as shown in FIG. 15A. This turning moves the end thereof into locking engagement with the cutting platform rod 108 maintaining the positioning of the cutting platform 107 relative to the proximal tibia.

Figures 16, 17:
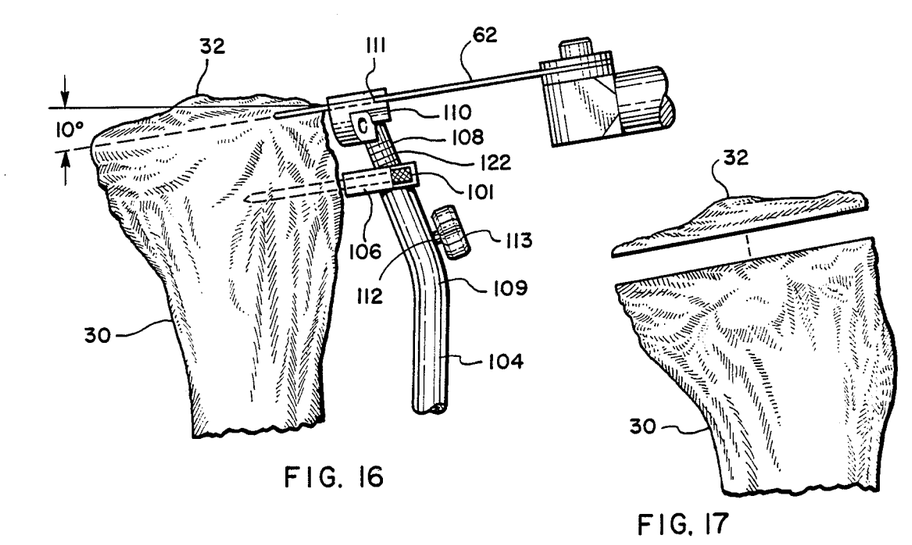
FIG. 16 shows a side elevation view of a saw blade fitted through the guide slot of the cutting platform of the tibial cutting guide shown operated to cut a flat surface across that proximal tibia at an angle of ten degrees (10°) below a plane across the distal tibia, which plane is perpendicular to the patient's mechanical axis.
FIG. 17 shows the proximal tibia end with a section shown separated therefrom.

The present invention thereby provides a tibial cutting guide 100 whose length can be adjusted between and fixed to points at the ankle and close to the proximal tibia. With the telescoping tube 104 and sleeve 103 fixed in place cutting platform 107 is independently positioned. So arranged, the cutting platform 107 positioning can be readily adjusted and re-adjusted without a disruption of the sleeve 103 and telescoping tube 104. The telescoping arrangement of cutting platform 110 thereby provides for positioning of the slot 110 or a top surface 110a thereof with respect to a plane across proximal tibia such that a certain thickness of resection or cut can be made thereacross with a saw blade 62 fitted through that slot or positioned on that flat surface 110a. After setting the cutting platform 110 to a desired position respective to that proximal tibia, the head end 113 of the bolt 112 is turned to move an end of that bolt into engagement with the cutting platform sliding rod 108, locking the cutting platform in place relative to that proximal tibia. Thereafter, saw blade 62, shown in FIG. 16, is fitted through slot 110 and reciprocated to cut across that bone end leaving a flat surface as illustrated in FIGS. 16 and 17.

FIGS. 15 and 15A show the cutting platform as including a tibial resection guide 115 that includes a lip 117 for fitting, as shown in FIG. 15, into an open end portion 111 of the slot 110 of the cutting platform 107. The tibial resection guide 115 consists of a cylindrical housing 116 wherefrom the lip 117 projects from proximate to a housing lower end at a normal angle to the cylinder vertical axis. The cylindrical housing is holed at opening 119, shown in broken lines in FIGS. 15 and 15A, proximate to its other cylindrical housing end, to receive a rod that is a resection depth gauge 118 fitted therethrough, which resection depth gauge is bent at 118a and terminates in a flat end. The flat gauge end is for proximal or distal travel over the bone end, the gauge body sliding along opening 119 to align with a deepest depression in that proximal tibia surface. The cutting platform 107 is then repositioned, rod 108 telescoped into sleeve 103 to move the depth gauge flat end into that deepest depression, setting thereby the depth of cut across the proximal tibia. A reciprocating saw blade 62 fitted through slot 110 is then operated to cut across that proximal tibia end surface, as illustrated in FIGS. 16 and 17. The tibia resection gauge 115 is, of course, provided for setting a depth of cut across that proximal tibia and so the flat end of the gauge 18 should be positioned in a lowest point in the bone surface. So arranged, when the cut is made, that cut will be two millimeters below that measured low point.

The above sets out the procedure for positioning the cutting platform 107 relative to the proximal tibia surface, whereat the bolt 112, as set out above, is turned at head end 113 into engagement with the cutting platform rod 108 to lock that cutting platform 107 in place. Additionally, as required, fixations pins 110b that are shown in broken lines in FIGS. 15 and 16 fitted through holes formed through the tabs 107a and turned into the tibia for securing or locking that cutting platform 110 in place. Thereafter, as illustrated in FIG. 16, the saw blade 62 is either fitted through the cutting platform slot 110 or is rested upon the cutting platform top 110a and is reciprocated to cut across that proximal tibia. A bone portion, as illustrated at 32 in FIG. 17, is thereby removed so as to leave a flat surface that is at a ten degree (10°) angle below a perpendicular plane to the patient's mechanical axis.

Should it be determined that a first cut across the proximal tibia is not deep enough, the cutting platform 107 can easily be reset by loosening of the bolt 112 and releasing any pinning of that cutting platform to the tibia. Thereafter, the cutting platform 107 can be further lowered to a desired level relative to distal femur end surface and bolt 112 again turned appropriately. As needed, the cutting platform can then be repinned to the tibia and additional bone removed to a desired depth across the proximal tibia. The surgeon, in making a determination of a required depth of a second cut can refit the tibia depth resection guide 115, as needed, to the cutting platform as illustrated in FIGS. 15 and 15A, keeping in mind that if such cut is made with blade 62 fitted through slot 110 it will be approximately two millimeters below that tibial depth resection guide flat end. Additionally, as shown best in FIG. 16, the telescoping cutting platform rod 108 can include calibrations 122 formed thereacross at spaced intervals for individual alignment with the end of the telescoping tube 104. Calibrations 122 are used to set a preferred spacing of the cutting platform 107 from the tube end. In practice, it has been found desirable that such calibrations 122 be spaced at two millimeters intervals from one another. So arranged, for making a second or even third cut of bone across the proximal tibia, a surgeon can set the depth of cut by reference to calibrations 122 and their relation to the telescoping tube 104 end without reference to the tibia depth resection guide.

Figure 18:
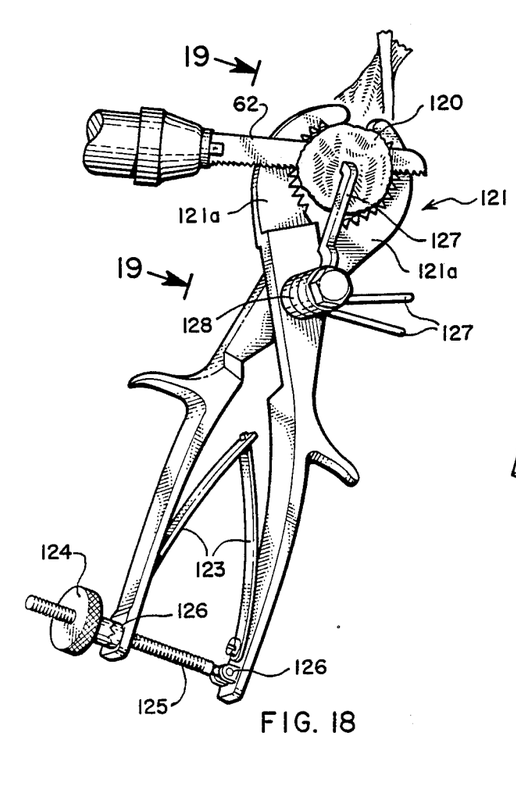
FIG. 18 shows a patella of the patient's knee maintained in a patellar cutting guide and shows a saw blade cutting longitudinally through that patella.
Figure 19:
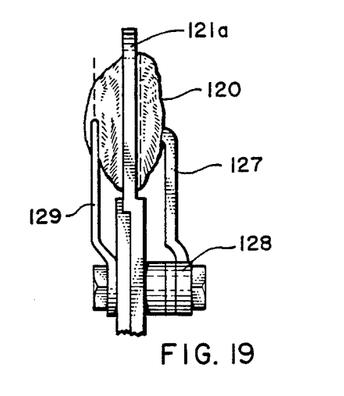
FIG. 19 is a side elevation view of the patellar cutting guide of FIG. 18 that includes a saw guide for setting the depth of cut thereacross.
Figure 20:
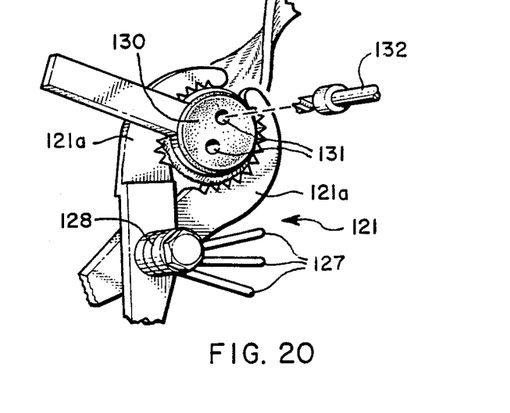
FIG. 20 shows the patella with a hole guide fitted over the cut surface thereof and shows a drill aligned to drill holes in that patella to receive a patella portion of a knee portion of a prosthesis fitted thereto.

Additional to the preparation of the distal femur and proximal tibia, in the preparation of a patient's knee for receiving a knee prosthesis, it is necessary to prepare the patella or knee cap. FIGS. 18, 19, and 20 illustrate a preferred procedure and apparatus for preparing the patella. The apparatus shown in Figs. 18, 19, and 20 is readily available and the techniques and procedures for its use are well known in the art. Such description as herein included merely is therefore supplied to provide a complete description of the system of the invention. In FIG. 18, the patella 120 is shown held in the jaws of a patellar cutting guide 121. Such patellar cutting guide is well known and in common use. In operation, a patella is positioned between jaws 121*a* of the guide and a pressure is established thereon by closing the jaws 120*a* thereof together. Jaws 121a can then be locked together against a biasing of a butting leaf spring arrangement 123 by appropriately turning a knurled nut 124 that is turned over a threaded rod 125 that is pivotally coupled to one patellar cutting guide handle 126 and is fitted through a hole formed through the other handle 126 end, the knurled nut 124 arranged beyond the hole formed through handle 126. Appropriate turning of knurled nut 124 thereby moves the handles 126 together, the jaws 121*a* squeezing the patella 120. Prior to locking the patella in place. a particular saw guide, shown in FIG. 19, is selected from a stack 128, the particular selected saw guide for a certain depth of resection, to pivot therefrom. This saw guide 127 will be selected as appropriate for the particular patella, to set the height thereof above jaws 121*a*. The surfaces of jaws 121*a* provide a rest for supporting a reciprocating saw blade 62 for cutting across that patella, as illustrated in FIG. 18. In practice, the patella is positioned such that it is on line with the patellar tendon, not shown, and has its surface to be resectioned contacting saw guide 127, as shown in FIG. 19.

In practice, with the patella held in the jaws 121*a*, the knurled nut 124 is turned on threaded rod 125 to move the ends of handles 126 together. The amount of patella to be resectioned is that portion that extends above the top of the saw guide jaws. This bone portion should be approximately equal on all sides and should be determined by palpitation or by visual inspection. On the undersurface of the patellar cutting guide 121, as illustrated in FIG. 19, is arranged a depth guide 129. The depth guide 129 is included as a safety feature to provide an indication as to whether sufficient bone stock will remain to attach a patella portion of the knee prosthesis after the resection cut is made. In practice, at least ten millimeters of patellar bone stock should remain to insure that the bone will accept fixation pegs of the patellar portion of the prosthesis. To insure that that at least a ten millimeter thickness remains after the cut, depth guide 129 should be positioned such that it will engage the anterior surface of the patellar 120 as that patellar is rotated. While that patellar 120 is being rotated, if the depth gauge 129 hits the anterior surface thereof, then the surgeon will know that at least ten millimeters of bone stock will remain after the cut. Whereas, if the patellar passes beneath the anterior surface of the patella, then too much patella will be cut. If this is the situation, then the patellar saw guide must be repositioned such that some part of the anterior patellar will contact the ten millimeter gauge, as illustrated in FIG. 19.

As set out above, the patella 120 is cut to have a flat surface utilizing the reciprocating saw 62, shown in FIG. 18. Thereafter, a patellar drill guide 130 is selected and centered over the cut surface of the patella and holes 131 are drilled therein. Holes 131 are to be essentially parallel to the patellar mechanical axis. They should not be perpendicular to that patellar mechanical axis as they could thereby be positioned along the transverse axis and create a significant stress riser that would be a potential site of patella fracture. With the drill guide appropriately placed, as illustrated in FIG. 20, a conventional femoral patellar peg drill 132 is preferably used to drill the two holes 131.

Prepared, as set out above, the patella 120 is ready to receive a patellar portion of the knee prosthesis, not shown. This patella portion will include pegs for fitting into the drilled holes 131 and is later secured thereto as by cementing. Similarly, when properly fit to the prepared distal femur and proximal tibia the other components of the knee prosthesis are cemented in place.

With the bone surfaces prepared, as described above, a trial reduction utilizing the selected prosthesis components is attempted. In such trial reduction, the respective sizes of the tibial base and femoral components are carefully selected to cooperate with one another. The fitting of these components, like the description of the bone preparation set out above, is detailed. Accordingly, as the present invention is not directed to this fitting process and such description of the trial reduction are therefore not included herewith. Also, it should be understood, a practice of the present invention is not limited to a particular knee prosthesis though, as set out above, the Miller/Galante is preferred.

As set out herein, the present invention consists of certain orthopedic instruments or tooling and their use in preparing the distal femur and proximal tibia ends to receive components of a knee prosthesis. While the instruments are preferably utilized in the described sequence in the preparation procedure, the individual instruments for preparing the distal femur and proximal tibia can be utilized separately and independently from one another. It should therefore be understood that the present disclosure is made by way of example only and that variations are possible without departing from the subject matter coming within the scope of the following claims, which claims embody our invention.

We claim:

1. A system of instruments for shaping the distal femur and proximal tibia surfaces for knee replacement surgery comprising, for preparing the distal femur: a femoral alignment guide having a body for attachment across the distal femur, which body includes means for mounting other instruments thereto and an intramedullary rod means that extends therefrom for insertion into a hole drilled in the distal femur to intersect the femur intramedullary channel for referencing said femoral alignment guide positioning to said intramedullary channel; an anterior femoral cutting guide means for attachment to said femoral alignment guide that includes a saw blade guide means for guiding travel of a saw blade operated to cut across the anterior femoral condyles in a plane that is parallel to the patient's intramedullary channel; a distal femoral cutting guide that includes, a body with means for securing it to said femoral alignment guide at an angle from a right angle therebetween such that a saw blade guide means formed through said body will be at a right angle to the patient's mechanical axis that includes a pivot pin means that extends from the body of said distal femoral cutting guide for fitting in a pivot hole formed in the femoral alignment guide and a plurality of hole means formed in a side of the body of said femoral alignment guide, each said hole means angled from the vertical, progressively from larger to smaller or smaller to larger, and straight pin means for fitting through a selected hole means and for securing in an appropriate recess in said femoral alignment guide body; means for securing said body of said distal femoral cutting guide to the distal femur surface that is provided by removal of said anterior condyles, and means for shaping to square the anterior and posterior condyles to the plane of the distal femur after the end thereof has been resectioned to a plane that is at a right angle to the patient's mechanical axis; and, for preparing the proximal tibia: a tibial cutting guide consisting of, a sleeve that is open on one end to receive a tube telescoped therein and includes a spike means on the other end thereof for securing that sleeve end into the tibia at the ankle; means for connecting said tube end that is opposite to said telescoped coupling into the tibia near the proximal tibia; means for releasably maintaining the positioning of said sleeve relative to said tube; rod means mounting a cutting platform means on one end that is telescoped into said tube at its opposite end; means for releasably maintaining the positioning of said rod means relative to said tube; and said cutting platform means consists of a body that includes a saw guide for aligning a saw blade to the proximal tibia end so as to cut across that bone to provide a flat surface thereacross.

2. A system of instruments as recited in claim 1, wherein the femoral alignment guide body includes a flat undersurface for engaging the distal femur wherefrom the intramedullary rod extends at a right angle, and a central lateral slot formed thereacross for accommodating a shoe means of the anterior femoral cutting guide fitted therein as the releasable mounting; and hole means for receiving pin means fitted therethrough and into the distal femur.

3. A system of instruments as recited in claim 1, wherein the mounting means for securing the distal femoral cutting guide to the femoral alignment guide consists of a pivot pin means that extends from the body of said distal femoral cutting guide for fitting in a pivot hole formed in the femoral alignment guide and a plurality of hole means formed in said body, each said hole means angled from the vertical, progressively from larger to smaller or smaller to larger, and straight pin means for fitting through a selected hole means and for securing in an appropriate recess in said femoral alignment guide body.

4. A system of instruments as recited in claim 3, wherein the hole means in the femoral alignment guide body for receiving the straight pin means turned therein is a slot that is in registry with each said hole means to receive and couple to said straight pin means turned therein.

5. A system of instruments as recited in claim 4, wherein the plurality of hole means consist of five (5) individual holes formed through the distal femoral cutting guide body that are on line with one another, each said hole means numbered individually from three (3) to eight (8), with each said number identifying the angle the particular hole means is offset from a right angle to the undersurface of said distal femoral cutting guide.

6. A system of instruments as recited in claim 4, wherein the straight pin means includes a threaded end for turning in the slot in the femoral alignment guide, which slot includes ridge means formed therein that said threaded straight pin means threaded end is turned over.

7. A system of instruments as recited in claim 1, wherein the anterior femoral cutting guide includes a flat yoke that has co-planar spaced apart legs separated by a web, said web having an undersurface whereto a shoe means is centrally fixed for coupling to the femoral alignment guide such that said legs will extend alongside the femur anterior condyles, such that said legs and web are parallel to the femur intramedullary channel, which web uppersurface has a mast secured thereto to project outwardly at a right angle from the web center and includes a boom, the one end of which boom is connected thereto to extend at a right angle therefrom, said boom having a bend formed therein that is proximate to the opposite end, said boom end to extend beyond the anterior femoral condyles.

8. A system of instruments as recited in claim 1, further including for a distal femur end that has been resectioned to a flat surface that is at a right angle to the femur mechanical axis and with the femur anterior femoral condyles removed, a means for placement on the flat distal femoral end for determining from a measure of the distance thereacross, a size of a femoral component or portion of a knee prosthesis to be secured thereto.

9. A system of instruments as recited in claim 1, further including a femoral finishing guide means that includes a body with a flat undersurface for attachment across the flat sectioned distal femur end, which flat distal femur end is at a right angle to the patient's mechanical axis, said body further including slots formed from a top surface through said flat undersurface for receiving a saw blade fitted therethrough for resectioning the bone end to square to right angles the anterior and posterior condyles to the plane of the distal femur end and to form anterior and posterior chamfers therebetween; and means for attaching said femoral finishing guide means body to said sectioned distal femur end.

10. A system of instruments as recited in claim 1, wherein the tibial cutting guide rod means is bent at an angle of ten degrees (10°) to the vertical so as to tilt the cutting platform means towards the proximal tibia.

11. A system of instruments as recited in claim 1, wherein the means for maintaining the rod means relative to the tube of the tibial cutting guide is a screw that is threaded on one end and has a large head on the other end, which screw is turned through a threaded hole in said tube to engage said rod.

12. A system of instruments as recited in claim 1, wherein the means for connecting said tube end of the tibial cutting guide to the tibia is a strap that is secured to said tube end to extend thereacross and is holed to receive fastener means therethrough; and fastener means for fitting through said strap holes that are turned into said tibia for mounting said tibial cutting guide tube strap to said tibia.

13. A system of instruments as recited in claim 1, wherein the cutting platform means of the tibial cutting guide includes a rectangular body that is flat on a proximal tibia engaging surface thereof, is for mounting to the rod means end to extend at a right angle thereacross and includes a slot formed therethrough as the saw guide that is at a right angle to said rod means.

14. A system of instruments as recited in claim 13, wherein the rectangular body includes arcuate projections that extend from the opposite body ends in the plane of the flat surface thereof to be positioned above the tibia, which arcuate projections are each holed to receive a fastener means therethrough; and fastener means for individually fitting through a hole in each said arcuate projection for turning into the tibia.

15. A system of instruments as recited in claim 13, further including a tibial resection guide for mounting to the cutting platform means body that includes a cylindrical body with a lip means extending from one end thereof for fitting into an appropriate opening in said cutting platform means body, which cylindrical body is holed laterally to receive a depth gauge means fitted in sliding engagement therethrough to move an end thereof into alignment over a deepest depression in the proximal tibia.

16. A system of instruments as recited in claim 15, wherein the depth gauge means is a solid rod that is bent towards the proximal tibia at a point back from one end thereof, which end is slanted to a plane that is parallel to the plane of the cutting guide means slot and includes a large head secured to the opposite solid rod end.

17. Instruments for shaping the distal femur for knee replacement surgery where the femur anterior condyles have been removed leaving a flat surface that is parallel to the femur intramedullary channel, comprising a femoral alignment guide having a body for attachment across the distal femur, which body includes means for mounting other instruments thereto and an intramedullary rod means that extends from a flat undersurface of said femoral alignment guide body and is for insertion into a hole drilled in the distal femur to intersect the femur intramedullary channel; and a distal femoral cutting guide that includes a body with means for securing it to said femoral alignment guide at an angle thereto whereby a cutting guide slot means of said distal femoral cutting guide is perpendicular or at a right angle to the patient's mechanical axis, the distal femoral cutting guide further including a pivot pin means that extends from a body of said distal femoral cutting guide for fitting in a pivot hole formed in the femoral alignment guide and a pluralty of hole means formed in a side of said femoral alignment guide body that is at a right angle to said femoral alignment guide flat undersurface, each said hole means angled from the vertical, progressively from larger to smaller or smaller to larger, and straight pin means for fitting through one of the hole means and for securing in an appropriate recess in said femoral alignment guide body to join together said femoral alignment guide and distal femoral cutting guide.

18. Instruments for shaping the distal femur as recited in claim 17, wherein the hole means in the side of the femoral alignment guide body for receiving the straight pin means turned therein is a slot that is in registry with each said hole means to receive and couple to said straight pin means turned therein.

19. Instruments for shaping the distal femur as recited in claim 18, wherein the plurality of hole means consist of five (5) individual holes formed through the distal femoral cutting guide body that are on line with one another, each said hole means numbered individually from three (3) to eight (8), with each said number identifying the angle the particular hole means is offset from a right angle to the undersurface of said distal femoral cutting guide.

20. Instruments for shaping the distal femur as recited in claim 18, wherein the straight pin means includes a threaded end for turning in the slot in the femoral alignment guide, which slot includes ridge means formed therein that said threaded straight pin means threaded end is turned over.

21. Instruments for shaping the distal femur as recited in claim 17, wherein the means for securing the distal femoral cutting guide body to the femur surface are spaced holes formed through said body to individually receive pins fitted therethrough that are turned into the femur.

22. An instrument for shaping the proximal tibia for knee replacement surgery comprising, a tibial cutting guide that includes a sleeve that is open on one end to receive a tube telescoped therein and includes a spike means on the other end thereof for securing that sleeve end into the tibia at the ankle; means for connecting said tube end that is opposite to said telescoped coupling into the tibia near the proximal tibia; means for releasably maintaining the positioning of said sleeve relative to said tube; rod means that is bent at an angle of ten degrees (10°) to the vertical towards the proximal tibia and mounts a cutting platform means on one end that is telescoped into said tube at its opposite end; means for releasably maintaining the positioning of said rod means relative to said tube with the cutting platform means consisting of a rectangular body that is flat on a proximal tibia engaging surface thereof and includes a slot formed therethrough as a saw guide for aligning a saw blade to the proximal tibia end so as to cut across that bone to provide a flat surface thereacross which rectangular body includes arcuate projections that extend from the opposite body ends in the plane of the flat surface thereof to be positioned above the tibia that are each holed to receive a fastener means therethrough; and fastener means for individually fitting through a hole in each said arcuate projection for turning into the tibia.

23. A system of instruments as recited in claim 22, wherein the means for maintaining the rod means relative to the tube of the tibial cutting guide is a screw that is threaded on one end and has a large head on the other end, which screw is turned through a threaded hole in said tube to engage said rod.

24. A system of instruments as recited in claim 22, wherein the means for connecting said tube end of the tibial cutting guide to the tibia is a strap that is secured to said tube end to extend thereacross and is holed to receive fastener means therethrough; and fastener means for fitting through said strap holes that are turned into said tibia for mounting said tibial cutting guide tube strap to said tibia.

25. A system of instruments as recited in claim 22, further including a tibial resection guide for mounting to the cutting platform means body that includes a cylindrical body with a lip means extending from one end thereof for fitting into an appropriate opening in said cutting platform means body, which cylindrical body is holed laterally to receive a depth gauge means fitted in sliding engagement therethrough to move an end thereof into alignment over a deepest depression in the proximal tibia.

26. A system of instruments as recited in claim 22, wherein the depth gauge means is a solid rod that is bent towards the proximal tibia at a point back from one end thereof, which end is slanted to a plane that is parallel to the plane of the cutting guide means slot and includes a large head secured to the opposite solid rod end.

27. Instruments for shaping the distal femur for knee replacement surgery comprising a means for sectioning the distal femur at an angle reflective of a right angle to a patient's mechanical axis from a reference to the patient's intramedullary channel, that includes an intramedullary rod for insertion into the patient's intramedullary channel through a hole formed through the distal femur cutting guide means for attachment to said intramedullary rod end for aligning a cutting guide portion thereof to a plane across the distal femur, guiding a saw blade means in resectioning a flat surface thereacross that is perpendicular to the patient's mechanical axis; a femoral finishing guide that includes a flat undersurface to evenly rest on the prepared flat distal femur surface and incorporates positioning means that extends from that flat undersurface for squaring said finishing guide such that the intersection of lateral and longitudinal axis thereon will align with the center of the patient's intramedullary channel, the upper surface of said finishing guide including a pair of counter sunk holes that are each spaced equally from the finishing guide center and are aligned on its lateral axis, said counter sunk holes each for receiving a fastener means turned therethrough and into said distal femur, the head thereof turned into the femur to a point that is below the cutting guide upper surface, said finishing guide further including, lateral slots formed across said finishing guide upper surface, exiting said finishing guide undersurface to receive and guide a saw blade means passed therethrough that is operated to resection the anterior and posterior femoral surfaces squaring them to a right angle to said prepared distal femur surface and to cut chamfers from said resectioned surfaces to said distal femur prepared surface, said chamfer lateral slots to intersect said counter sunk holes at the counter sunk upper end of each; and the fastener means is a peg means with a head end to travel into said counter sunk hole to below the level of the chamfer lateral slots, said peg means to be removable to allow the holes formed in the distal femur surface to receive projections from a knee prosthesis undersurface securing said knee prosthesis thereto.

28. Instruments for shaping the distal femur for knee replacement surgery as recited in claim 27, further including an alignment guide means that is secured to the intramedullary rod end for mounting an anterior femoral cutting guide means that is for guiding a saw blade used for resectioning the femur anterior condyles so as to leave a bone surface that is parallel to the patient's intramedullary channel, and for mounting the distal femur cutting guide means, which said distal femur cutting guide means mounting provides for setting a saw guide portion of said distal femur cutting guide means at an angle to the patient's intramedullary channel that is perpendicular to the patient's mechanical axis.

29. Instruments for shaping the distal femur for knee replacement surgery as recited in claim 28, further including an anterior and posterior measuring guide means having a body that includes a flat undersurface for fitting over the resectioned distal femur, a means fixed to extend at a normal angle from a lower surface thereof for contacting the distal femur posterior condyles, and a gauge means that consists of flat slide portion dimensions to fit and slide freely within a center slot formed longitudinally in the anterior and posterior measuring guide means body extending from a flat upper surface thereof, said slide portion including a scale on one face thereof with graduations to be individually aligned with the anterior and posterior measuring guide means body flat surface as said slide portion is moved within said anterior and posterior measuring guide means body center slot, said slide portion opposite face, proximate to an end thereof, including a post means that extends at a right angle therefrom to engage a resectioned surface of the distal femur wherefrom the anterior condyles have been removed; and means for releasably maintaining said slide portion in said center slot of said anterior and posterior measuring guide means body.

30. Instruments for shaping the distal femur for knee replacement surgery as recited in claim 27, wherein the femur finishing guide has a rectangular shape with a flat undersurface and includes a ledge means that extends outwardly from along an upper edge of that flat undersurface and is angled from that flat undersurface so as to fit snugly against the resectioned surface of the anterior condyles; and the finishing guide lateral slots are formed parallel to one another and to said ledge means each slot extending from the short rectangular sides and are closed at the center axis.

* * * * *

UNITED STATES PATENT AND TRADEMARK OFFICE
CERTIFICATE OF CORRECTION

PATENT NO. : 4,759,350
DATED : July 26, 1988
INVENTOR(S) : Harold K. Dunn, et al.

It is certified that error appears in the above-identified patent and that said Letters Patent is hereby corrected as shown below:

Column 6, line 19, after "across the" delete "distal" and substitute --proximal--.

Column 19, line 4, after "of said" delete "femoral alignment guide" and insert, --distal femoral cutting guide--.

Column 21, line 43, after "said" delete "femoral alignment guide" and insert --distal femoral cutting guide--.

Column 23, line 8, after "femur" add, --to intersect the femur intramedullary channel; a distal femur--.

Signed and Sealed this

Twentieth Day of December, 1988

Attest:

DONALD J. QUIGG

Attesting Officer   Commissioner of Patents and Trademarks